United States Patent
Sinha

(10) Patent No.: US 6,718,269 B2
(45) Date of Patent: Apr. 6, 2004

(54) APPARATUS, PROGRAM PRODUCT AND METHOD OF ESTIMATING THE STRESS INTENSITY FACTOR RATIO OF A MATERIAL

(75) Inventor: Arvind Kumar Sinha, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 103 days.

(21) Appl. No.: 10/022,779

(22) Filed: Dec. 13, 2001

(65) Prior Publication Data

US 2003/0114998 A1 Jun. 19, 2003

(51) Int. Cl.⁷ ................................. G01L 1/00
(52) U.S. Cl. ........................... 702/42; 73/794
(58) Field of Search .................. 702/35, 42, 43; 73/799, 794, 788, 783, 767, 763

(56) References Cited

U.S. PATENT DOCUMENTS

| | | | |
|---|---|---|---|
| 4,418,563 A | 12/1983 | Kalthoff et al. | 73/12 |
| 5,317,925 A | 6/1994 | Hayashi et al. | 73/799 |
| 5,641,912 A | 6/1997 | Manahan, Sr. | 73/797 |

FOREIGN PATENT DOCUMENTS

| | | | | |
|---|---|---|---|---|
| JP | 363066428 A | * | 3/1988 | G01L/1/00 |

* cited by examiner

Primary Examiner—John Barlow
Assistant Examiner—Stephen J. Cherry
(74) Attorney, Agent, or Firm—Matthew J. Bussan

(57) ABSTRACT

An apparatus, program product, and method for estimating the stress intensity factor ratio (SIFR) of a material. The material is supported on a support and a load is applied to the material using a load member. A pair of strain components are measured using a strain gage attached to the material, and are stored in memory. The strain gage may be a rosette strain gage, for example. A processor calculates a ratio of the stored pair of strain components to thereby provide an estimate of the SIFR of the material. Advantageously, this estimate of the SIFR of the material is readily provided. Also advantageously, the estimate may be provided in a manner that is non-destructive to the material. The processor may additionally calculate the stress level of the material based on the estimated SIFR.

8 Claims, 5 Drawing Sheets

APPARATUS, PROGRAM PRODUCT AND METHOD OF ESTIMATING THE STRESS INTENSITY FACTOR RATIO OF A MATERIAL

FIELD OF THE INVENTION

The present invention relates in general to the determination of physical properties of materials. More particularly, the present invention relates to an apparatus, program product and method of estimating the stress intensity factor ratio (SIFR) of a material.

BACKGROUND

The development of the EDVAC computer system of 1948 is often cited as the beginning of the computer era. Since that time, computer systems have evolved into extremely sophisticated devices, and computer systems may be found in many different environments. Since the dawn of the computer age, the performance of computers has been measured to determine how well the computer performs certain tasks. One measure of computer performance is reliability, availability and serviceability (RAS). The physical properties of materials used in, or contemplated for use in, components of computer systems are often evaluated to increase the RAS of the computer systems. For example, computer systems typically contain numerous electronic circuit boards, such as a multi-layered electronic backplane. A thermal or mechanical failure of a material used in the electronic circuit board can decrease the RAS of the computer system in which the board is installed.

Consequently, materials used in, or contemplated for use in, components of computer systems are typically subjected to testing mechanisms to evaluate their physical properties such as fracture toughness, i.e., an inherent material property which describes the resistance to a fracture. For example, a hardness tester may be employed to evaluate a material's fracture toughness. A hardness tester subjects the component to a load. Typically, the load is increased until the component fractures. This testing mechanism is undesirable for a number of reasons. Firstly, hardness testers typically subject the component to a destructive test. Components such as multi-layered electronic backplanes are relatively costly and their destruction adds to the cost of computer systems. Secondly, hardness testers typically do not provide the stress intensity factor ratio (SIFR) of the material under evaluation. The SIFR is the ratio of a shear (mode 2) stress intensity factor $K_2$ over a normal (mode 1) stress intensity factor $K_1$ (SIFR=$K_2/K_1$). Knowledge of the SIFR is advantageous in the evaluation of the material, e.g., knowledge of the SIFR allows calculation of the stress level. However, the SIFR is typically not provided by hardness testers at least in part because of the relative complexity of the measurements and calculations heretofore necessary for its generation.

Therefore, there exists a need to provide an enhanced testing mechanism that readily provides the SIFR of a material under evaluation. There also exists the need for such an enhanced testing mechanism that is preferably non-destructive to the material under evaluation.

SUMMARY OF THE INVENTION

An object of the present invention is to provide an enhanced material testing mechanism that addresses these and other problems associated with the prior art.

These and other objects of the present invention are achieved by providing an apparatus, program product, and method for estimating the stress intensity factor ratio (SIFR) of a material. The material is supported on a support and a load is applied to the material using a load member. A pair of strain components are measured using a strain gage attached to the material, and are stored in memory. The strain gage may be a rosette strain gage, for example. A processor calculates a ratio of the stored pair of strain components to thereby provide an estimate of the SIFR of the material. Advantageously, this estimate of the SIFR of the material is readily provided. Also advantageously, the estimate may be provided in a manner that is non-destructive to the material.

In one case, the pair of strain components in a polar coordinate system are radial strain $\epsilon_{rr}$ and axial strain $\epsilon_{\theta\theta}$, and the ratio of the pair of strain components is $\epsilon_{rr}/\epsilon_{\theta\theta}$. In an alternative case, the pair of strain components in a Cartesian coordinate system are shear strain $\epsilon_{xy}$ and normal strain $\epsilon_{yy}$, and the ratio of the pair of strain components is $\epsilon_{xy}/\epsilon_{yy}$.

The processor may additionally calculate the stress level of the material based on the estimated SIFR. The stress level of the material may be calculated as $\sigma$=SIFR $(\epsilon E)$, $\sigma$ being the stress level of the material, SIFR being the estimated stress intensity factor ratio, $\epsilon$ being the strain of the material, and E being Young's modulus of the material.

BRIEF DESCRIPTION OF THE DRAWINGS

The present invention together with the above and other objects and advantages can best be understood from the following detailed description of the embodiments of the invention illustrated in the drawings, wherein like reference numerals denote like elements.

DETAILED DESCRIPTION OF THE PREFERRED EMBODIMENTS

Hardware and Software Environment

Figure 1:
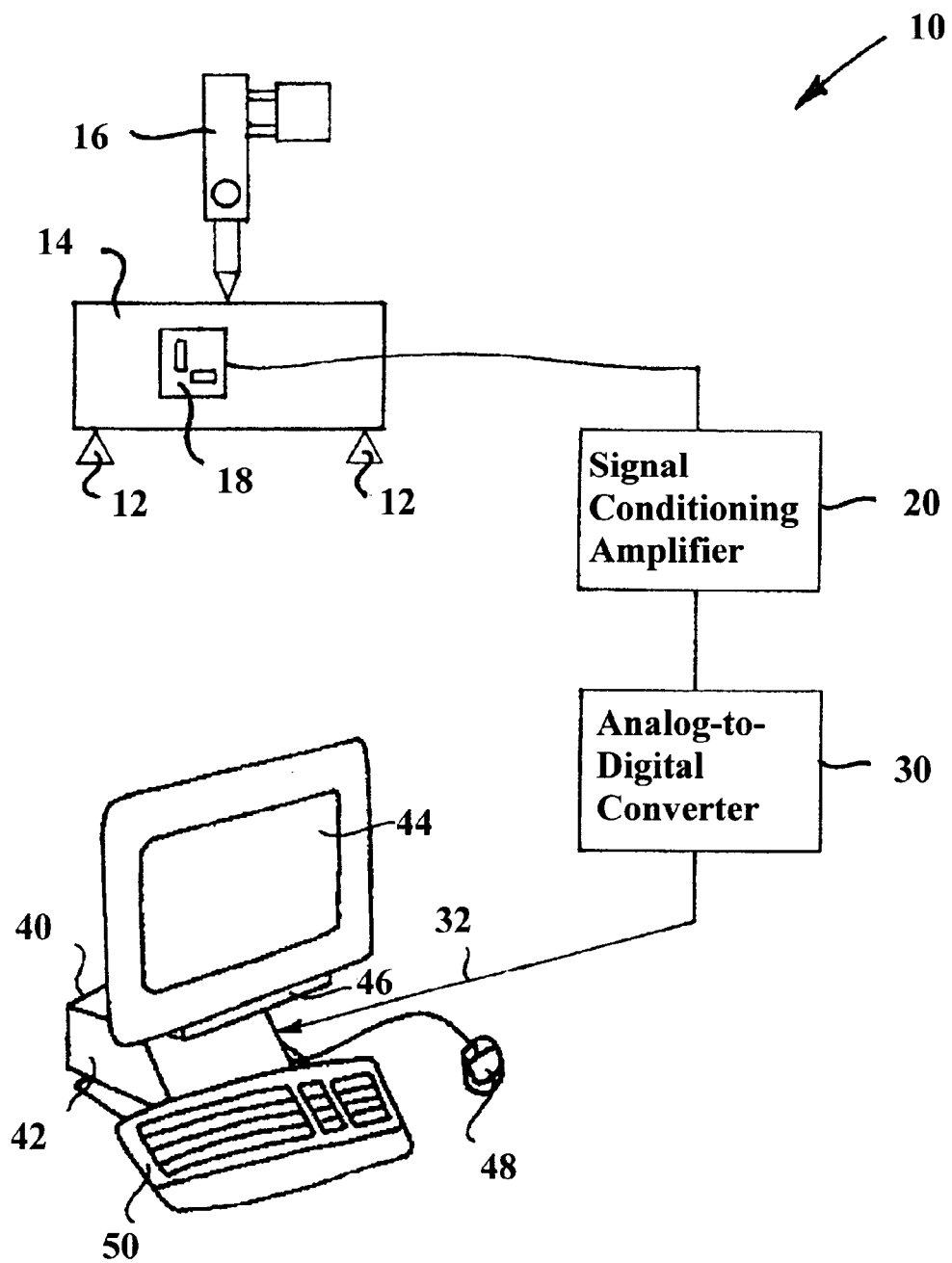
FIG. 1 is a block diagram of an apparatus for estimating the stress intensity factor ratio of a material consistent with the present invention.

FIG. 1 illustrates an apparatus 10 for estimating the stress intensity factor ratio (SIFR) of a material consistent with the present invention. Apparatus 10 includes two spaced apart supports 12 upon which rests a material 14 that is to undergo testing. Material 14 may be an electronic circuit board (e.g., a multi-layered electronic backplane), an electronic connector, a fastener, a structural component, an aerospace component or any other material having a flaw. Supports 12 are shown in FIG. 1 for the purpose of illustration and not limitation. Any suitable type, number and arrangement of supports 12 may be used. A load is applied to material 14 at a point that is preferably directly over a flaw in material 14. The support points and load point may form an ASTM specified three point bend configuration, for example. As shown in FIG. 1, the load may be applied by a hardness tester 16. Hardness tester 16, however, is shown for the purpose of illustration and not limitation. Other conventional devices may by used in lieu of a hardness tester to apply the load.

A strain gage 18 is attached to material 14 to measure at least a pair of strain components, as discussed in more detail below. Strain gage 18 is attached to material 14 at a point that is preferably near the flaw in material 14. Strain gage 18 is at least biaxial, such as a rosette strain gage having two or more independent grids for making measurements of strain along each of their axes about a common point. Such strain gages and the techniques by which they are attached are conventional and well known in the art. For example, strain gage 18 may be a three-element 45° rectangular stacked rosette strain gage, such as strain gage model number WA-XX-060WR-120, available from Micro-Measurements Division of Vishay Measurements Group, Inc., Raleigh, N.C.

Strain gage 18 is connected to a signal conditioning amplifier 20 which conditions and amplifies low-level signals from strain gage 18 to generate high-level signals. The signal conditioning provided by signal conditioning amplifier 18 may include signal filtering. Signal conditioning amplifiers are conventional and well known in the art. For example, signal conditioning amplifier 20 may be a 2300 System with 2310/2311 Signal Conditioning Amplifier Modules, available from Vishay Measurements Group, Inc., Raleigh, N.C.

The high-level signals generated by signal conditioning amplifier 20 are provided to an analog-to-digital converter 30. Analog-to-digital converter 30 may include hardware and/or software for converting analog signals generated by signal conditioning amplifier 20 to digital signals. Analog-to-digital converters are conventional and well known in the art. For example, analog-to-digital converter 30 may be a Model 2000 Analog-to-Digital Converter, available from Vishay Measurements Group, Inc., Raleigh, N.C.

The digital signals from analog-to-digital converter 30 are transferred to a computer 40 through a suitable connection 32, such as an IEEE-488 general purpose interface bus (GPIB). Computer 40 includes one or more computers, e.g., desktop or PC-based computer, workstation, a PC-based server, a minicomputer, a midrange computer, a mainframe computer, etc. Computer 40 may be networked to any number of other computers and other devices through a network interconnection, such as a local-area network (LAN), a wide-area network (WAN), a wireless network, and a public network (e.g., the Internet).

Computer 40 may include a central processing unit (CPU) 42; a number of peripheral components such as a computer display 44; a storage device 46; and various input devices (e.g., a mouse 48 and a keyboard 50), among others. Although signal conditioning amplifier 20, analog-to-digital converter 30 and computer 40 are shown in FIG. 1 as three separate components, they may be configured as any number of components. For example, the hardware and/or software for performing functions of signal conditioning amplifier 20 and analog-to-digital converter 30 may be integrated into an enhanced version of computer 40. Alternatively, the hardware and/or software for performing functions of computer 40 may be integrated into an enhanced version of analog-to-digital converter 30. In another alternative embodiment, the hardware and/or software for performing functions of signal conditioning amplifier 20, analog-to-digital converter 30 and computer 40 may be integrated into an enhanced version of hardness tester 16.

Figure 2:
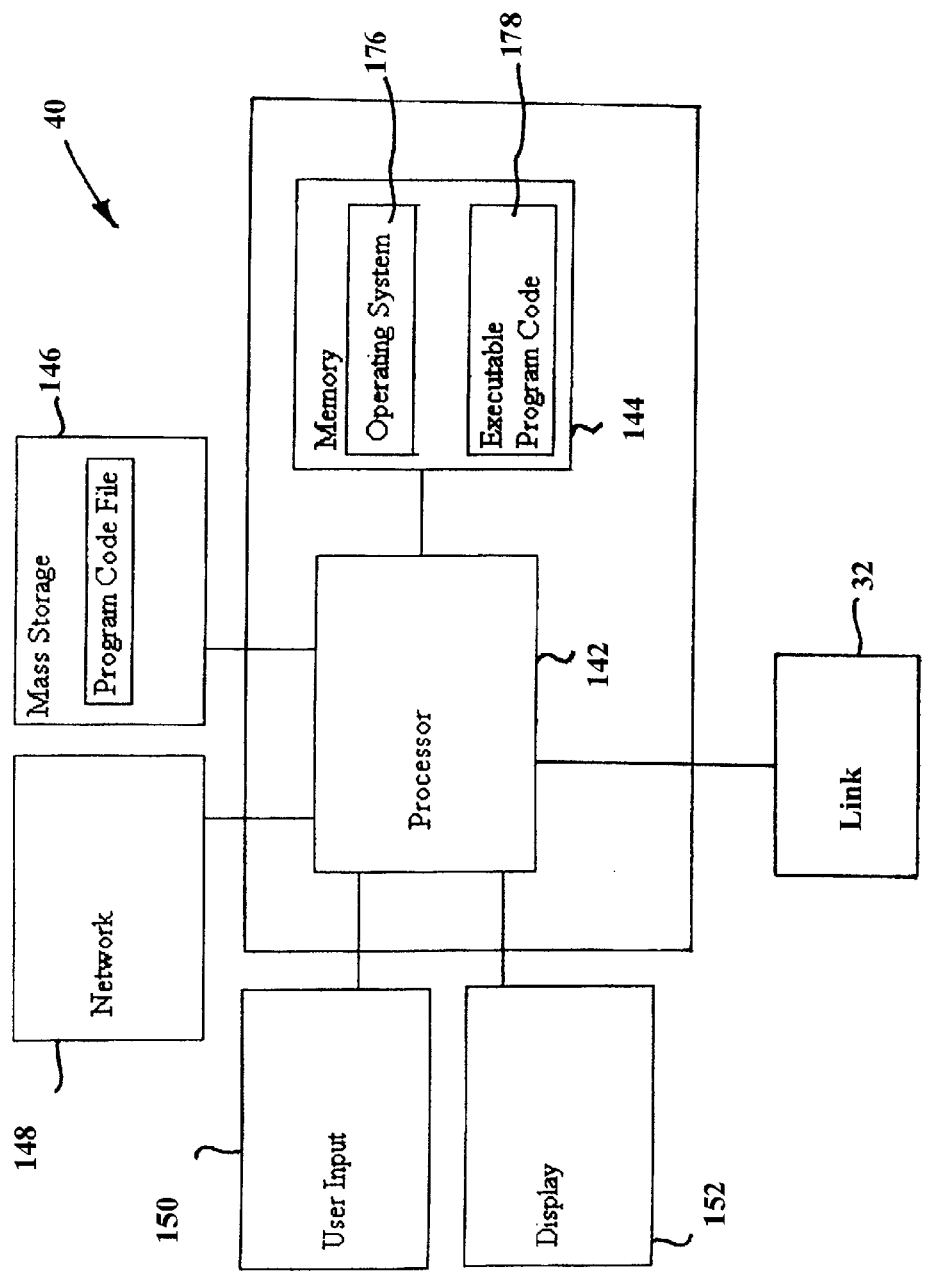
FIG. 2 is a block diagram of an exemplary hardware and software environment for a computer shown in FIG. 1.

FIG. 2 illustrates in another way an exemplary hardware and software environment for an computer 40 consistent with the present invention. For the purposes of the present invention, computer 40 may represent practically any type of computer, computer system or other programmable electronic device, including a client computer, a server computer, a portable computer, an embedded controller, etc. Computer 40 may be coupled in a network, or may be a stand-alone device in the alternative. Computer 40 will hereinafter also be referred to as a "computer", although it should be appreciated the term "computer" may also include other suitable programmable electronic devices consistent with the present invention.

Computer 40 typically includes at least one processor 142 coupled to a memory 144. Processor 142 may represent one or more processors (e.g., microprocessors), and memory 144 may represent the random access memory (RAM) devices comprising the main storage of computer 140, as well as any supplemental levels of memory, e.g., cache memories, non-volatile or backup memories (e.g., programmable or flash memories), read-only memories, etc. In addition, memory 144 may be considered to include memory storage physically located elsewhere in computer 140, e.g., any cache memory in a processor 142, as well as any storage capacity used as a virtual memory, e.g., as stored on a mass storage device 146 or on another computer coupled to computer 140 via a network. Likewise, memory 144 may be considered to include memory physically located in analog-to-digital converter 30 and accessed via connection 32.

Computer 40 also typically receives a number of inputs and outputs for communicating information externally. For interface with a user or operator, computer 40 typically includes one or more user input devices 150 (e.g., a keyboard, a mouse, a trackball, a joystick, a touchpad, and/or a microphone, among others) and a display 152 (e.g., a CRT monitor, an LCD display panel, and/or a speaker, among others). It should be appreciated, however, that with some implementations of computer 40, e.g., some server computer implementations, direct user input and output may not be supported by the computer.

For additional storage, computer 40 may also include one or more mass storage devices 146, e.g., a floppy or other removable disk drive, a hard disk drive, a direct access storage device (DASD), an optical drive (e.g., a CD drive, a DVD drive, etc.), and/or a tape drive, among others. Furthermore, computer 40 may include an interface with one or more networks 148 (e.g., a LAN, a WAN, a wireless network, and/or the Internet, among others) to permit the communication of information with other computers coupled to the network. In addition, computer 40 includes an interface with link 32 to permit communication of information with analog-to-digital converter 30 coupled to link 32.

It should be appreciated that computer 40 typically includes suitable analog and/or digital interfaces between processor 142 and each of memory 144, mass storage device 146, network 148, user input device 150, display 152 and link 32, as is well known in the art.

Computer 40 operates under the control of an operating system 176, and executes various computer software applications, components, programs, objects, modules, etc. (e.g., executable program 178, among others). Moreover, various applications, components, programs, objects, modules, etc. may also execute on one or more processors in another computer coupled to computer 40 via network 148, e.g., in a distributed or client-server computing environment, whereby the processing required to implement the functions of a computer program may be allocated to multiple computers over a network.

In general, the routines executed to implement the embodiments of the invention, whether implemented as part of an operating system or a specific application, component, program, object, module or sequence of instructions will be referred to herein as "computer programs", or simply "programs". The computer programs typically comprise one or more instructions that are resident at various times in various memory and storage devices in a computer, and that, when read and executed by one or more processors in a computer, cause that computer to perform the steps necessary to execute steps or elements embodying the various aspects of the invention. Moreover, while the invention has and hereinafter will be described in the context of fully functioning computers and computer systems, those skilled in the art will appreciate that the various embodiments of the invention are capable of being distributed as a program product in a variety of forms, and that the invention applies equally regardless of the particular type of signal bearing media used to actually carry out the distribution. Examples of signal bearing media include but are not limited to recordable type media such as volatile and non-volatile memory devices, floppy and other removable disks, hard disk drives, optical disks (e.g., CD-ROM's, DVD's, etc.), among others, and transmission type media such as digital and analog communication links.

In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

Those skilled in the art will recognize that the exemplary environments illustrated in FIGS. 1 and 2 are not intended to limit the present invention. Indeed, those skilled in the art will recognize that other alternative hardware and/or software environments may be used without departing from the scope of the invention.

Exemplary Material System

Figure 3:
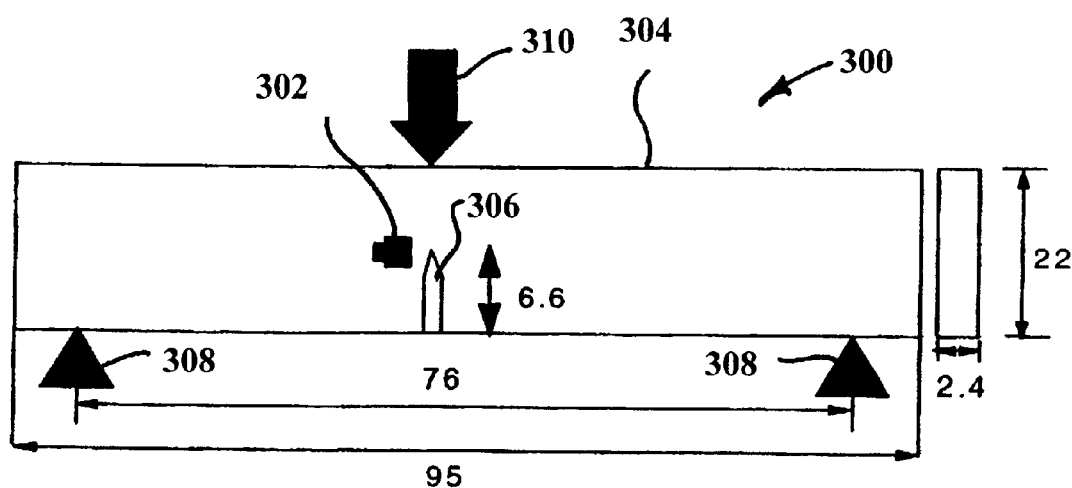
FIG. 3 is a front view and a side view of an exemplary material system consistent with the present invention.

An exemplary test station 300 is shown in FIG. 3. The exemplary test station 300 is configured with a strain gage 302 attached to a notched sample 304 consistent with the present invention. Exemplary test station 300 is shown for the purpose of illustration and not limitation. Other materials may be tested in lieu of notched sample 304. In this example, each notched sample 304 was approximately 95 mm wide, 22 mm high and 2.4 mm thick. Three nearly identical notched samples 304 were cut from epoxy-based multilayered electronic backplanes using a diamond edge wheel and cleaned using isopropyl alcohol. The notched samples 304 are referred to as "notched" because a crack 306 having a specified geometry was cut into each, i.e., the crack length was 6.6 mm. Notched samples 304 were tested individually, each resting on supports 308 that were spaced apart by 76 mm. A load 310 of 100 N was applied to notched sample 304 at a point that was directly over crack 306. The dimensions of the material to be tested, the crack geometry (or defect geometry), the support spacing, the load and its application point are set forth in this example for purpose of illustration and not limitation. For example, each of these parameters may be changed to a suitable value for the particular material to be tested.

Figure 4:
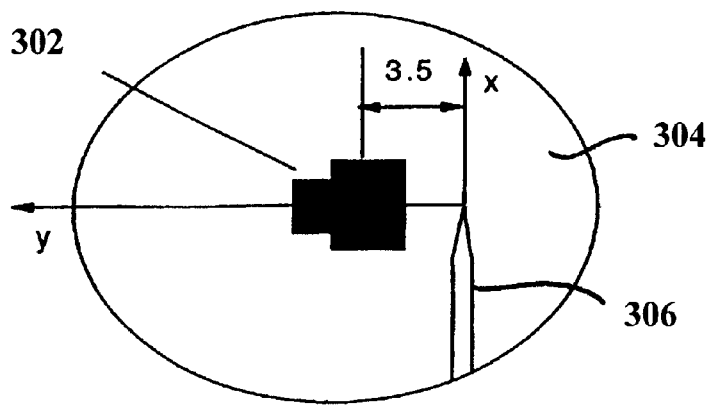
FIG. 4 is an enlarged view showing an exemplary placement of a strain gage in the material system shown in FIG. 3.

FIG. 4 is an enlarged view showing an exemplary placement of strain gage 302 on notched sample 304. Strain gage 302 was attached to notched sample 304 so that the "common point" of the grid axes of strain gage 302 was 3.5 mm from the tip of crack 306 in the width direction (y-axis) and aligned with the tip of crack 306 in the height direction (x-axis). Strain gage 302 was a biaxial rosette strain gage having two independent grids for making measurements of strain along each of their axes about the "common point" and having a gage length 0.55 mm. The gage type, length and placement are set forth in this example for purpose of illustration and not limitation. Different gage types, gage lengths and placements of the strain gage near the crack tip (or defect) may be suitable depending on the particular material to be tested, for example.

Estimating the Stress Intensity Factor Ratio

Figure 5:
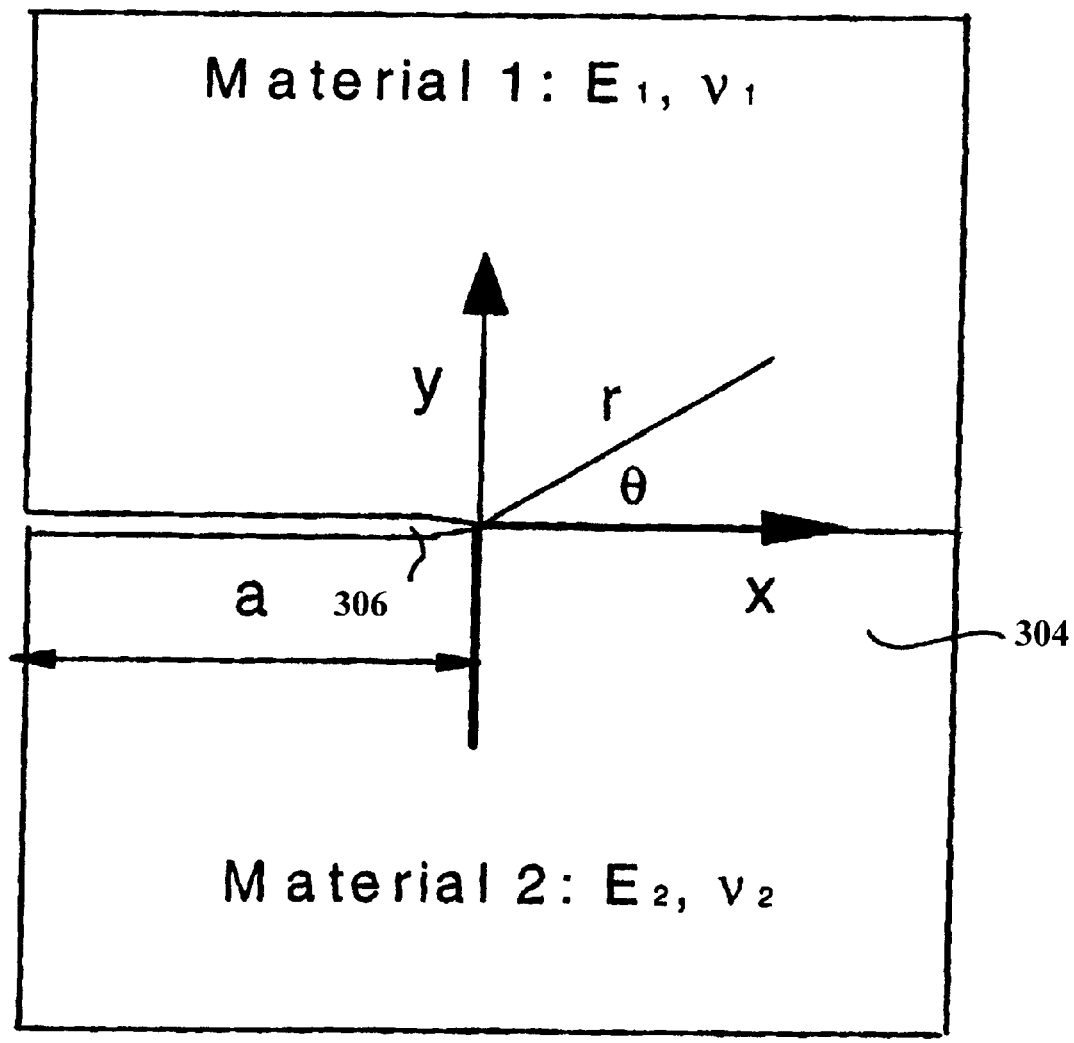
FIG. 5 is an enlarged view showing exemplary Cartesian and polar coordinate systems in the material system shown in FIG. 3.

The present invention makes it possible to readily provide an estimate of stress intensity factor ratio (SIFR) of a material. The SIFR is the ratio of a shear (mode 2 failure) stress intensity factor $K_2$ over a normal (mode 1 failure) stress intensity factor $K_1$ (SIFR=$K_2/K_1$). Referring now to FIG. 5, which is an enlarged view showing exemplary arrangements of Cartesian and polar coordinate systems on notched sample 304, the shear stress intensity factor $K_2$ over the normal stress intensity factor $K_1$ is proportional to the shear stress $\sigma_{xy}$ over the normal stress $\sigma_{yy}$, which is proportional to the shear strain $\sigma_{xy}$ over the normal strain $\sigma_{yy}$, which is proportional to the radial strain $\epsilon_{rr}$ over the axial strain $\epsilon_{\theta\theta}$ (SIFR=$K_2/K_1 \propto \sigma_{xy}/\sigma_{yy} \propto \epsilon_{xy}/\epsilon_{yy} \propto \epsilon_{rr}/\epsilon_{\theta\theta}$). The radial strain $\epsilon_{rr}$ and axial strain $\epsilon_{\theta\theta}$ are readily measured using a strain gage through well known techniques. Because these techniques are well known they are not presented herein. The present invention takes advantage of the fact that these strain components may be easily measured, and that an estimation of the SIFR of a material may be provided based on the calculation of the ratio of $\epsilon_{rr}/\epsilon_{\theta\theta}$.

It should be appreciated that the shear strain $\epsilon_{xy}$ and the normal strain $\epsilon_{yy}$ may also be readily measured using a strain gage through well known techniques. Thus, the estimate of the SIFR of a material may also be based on calculation of the ratio of $\epsilon_{xy}/\epsilon_{yy}$.

Referring back to FIG. 2, executable program code 178 in memory 144 includes a program that is capable of executing on processor 142. The program may be recorded on mass storage 146, or some other signal bearing media, as a program code file and transferred to memory 144 for faster access by processor 142. The program stores in memory, e.g., memory 144, a pair of strain components, e.g., $\epsilon_{rr}$ and $\epsilon_{\theta\theta}$, measured using a strain gage attached to the material. As mentioned above, the pair of strain components are measured using known techniques. The pair of strain components may be directly provided to processor 142 by analog-to-digital converter 30 (shown in FIG. 1) through link 32. Alternatively, the pair of strain components may be calculated by processor 142 based on the digital signals transferred to processor 142 by analog-to-digital converter 30 through link 32. The program also calculates a ratio of the stored pair of strain components, e.g., $\epsilon_{rr}/\epsilon_{\theta\theta}$, to thereby provide an estimate the SIFR of the material.

Knowledge of the SIFR is advantageous in the evaluation of the material. For example, knowledge of the SIFR allows calculation of the stress levels around the crack tip due to thermal and/or mechanical fatigue. That is, the stress level of the material may be calculated by the program as σ=SIFR (εE), where σ is the stress level of the material, SIFR is the estimated stress intensity factor ratio, $\epsilon$ is the strain of the material, and E is the Young's modulus of the material.

Because the present invention estimates the SIFR of a material based on readily measured strain components, the present invention is simple to use. Moreover, the present invention can be implemented for a variety of materials (i.e., strain gages may be typically be attached to any material) and in a variety of operating temperatures (i.e., strain gages may be used to measure strain components at temperatures up to 250° F. or more).

Figure 6:
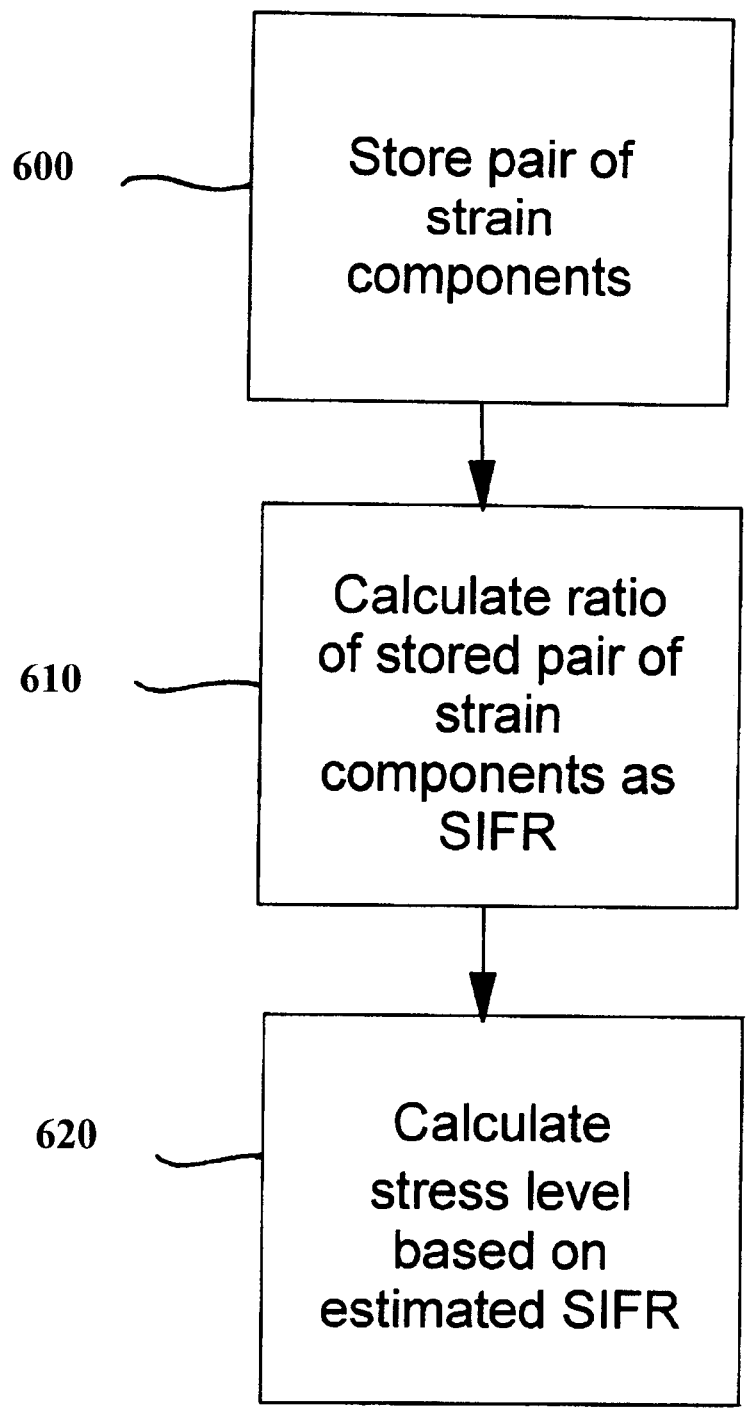
FIG. 6 is a flow diagram illustrating steps for estimating the stress intensity factor ratio and stress level of a material consistent with the present invention.

FIG. 6 is a flow diagram illustrating steps for estimating the stress intensity factor ratio and stress level of a material consistent with the present invention. At block 600, the process begins with the step of storing in a memory, e.g., memory 144, a pair of strain components, e.g., $\epsilon_{rr}$ and $\epsilon_{\theta\theta}$, measured using a strain gage attached to the material. At block 610, the process continues with the step of calculating a ratio of the stored pair of strain components, e.g., $\epsilon_{rr}/\epsilon_{\theta\theta}$, to thereby provide an estimate the stress intensity factor ratio of the material. At block 620, the process may optionally continue by additionally calculating a stress level of the material as $\sigma$=SIFR ($\epsilon$E), $\sigma$ being the stress level of the material, SIFR being the estimated stress intensity factor ratio, $\epsilon$ being the strain of the material, and E being Young's modulus of the material.

Referring back to the example above, estimates of the SIFR for each of the three notched samples were made based on strain gage measurements according to the present invention, and the results are presented in the table below. Also presented in the table are estimates of SIFR made according to a finite element analysis (FEA) model of the material system. The similar results indicate that the present invention is a viable tool of estimation of SIFR.

| | Test Data | | | FEA Data | | |
|---|---|---|---|---|---|---|
| Sample # | $\epsilon_{rr}$ ($\mu\epsilon$) | $\epsilon_{\theta\theta}$ ($\mu\epsilon$) | SIFR ($\epsilon_{rr}/\epsilon_{\theta\theta}$) | $\epsilon_{rr}$ ($\mu\epsilon$) | $\epsilon_{\theta\theta}$ ($\mu\epsilon$) | SIFR ($\epsilon_{rr}/\epsilon_{\theta\theta}$) |
| 1 | 526 | 1153 | 0.46 | 450 | 1166 | 0.39 |
| 2 | 539 | 1175 | 0.46 | 476 | 1188 | 0.40 |
| 3 | 524 | 1150 | 0.45 | 468 | 1163 | 0.40 |

While this invention has been described with respect to the preferred and alternative embodiments, it will be understood by those skilled in the art that various changes in detail may be made therein without departing from the spirit, scope, and teaching of the invention. Accordingly, the herein disclosed invention is to be limited only as specified in the following claims.

What is claimed is:

1. An apparatus for estimating the stress intensity factor ratio of a material, the apparatus comprising:
    a support for supporting the material;
    a load member for applying a load to the material;
    a strain gage attached to the material to measure at least a pair of strain components;
    a processor that calculates a ratio of the pair of strain components to thereby provide an estimate the stress intensity factor ratio of the material, the stress intensity factor then being used to calculate a stress level of the material.

2. The apparatus as recited in claim 1, wherein the stress level of the material is calculated as $\sigma$=SIFR ($\epsilon$E), $\sigma$ being the stress level of the material, SIFR being the estimated stress intensity factor ratio, $\epsilon$ being the strain of the material, and E being Young's modulus of the material.

3. A computer-implemented method of estimating the stress intensity factor ratio of a material, wherein the material is supported on a support and a load member applies a load to the material, the computer-implemented method comprising the steps of:
    storing in a memory associated with a computer a pair of strain components, the pair of strain components being measured using a strain gage attached to the material;
    calculating in a processor associated with the computer a ratio of the stored pair of strain components to thereby provide an estimate the stress intensity factor ratio of the material, and
    calculating in the processor a stress level of the material based on the estimated stress intensity factor ratio.

4. The computer-implemented method as recited in claim 3, wherein the stress level of the material is calculated as $\sigma$=SIFR ($\epsilon$E), $\sigma$ being the stress level of the material, SIFR being the estimated stress intensity factor ratio, $\epsilon$ being the strain of the material, and E being Young's modulus of the material.

5. A program product for estimating the stress intensity factor ratio of a material, the program product comprising:
    a signal bearing media; and
    a program recorded on the signal bearing media, the program being capable of executing on a processor associated with a computer, the program storing in a memory associated with the computer a pair of strain components measured using a strain gage attached to the material and calculating a ratio of the stored pair of strain components to thereby provide an estimate the stress intensity factor ratio of the material, the stress intensity factor then being used to calculate a stress level of the material.

6. The apparatus as recited in claim 5, wherein the stress level of the material is calculated as $\sigma$=SIFR ($\epsilon$E), $\sigma$ being the stress level of the material, SIFR being the estimated stress intensity factor ratio, $\epsilon$ being the strain of the material, and E being Young's modulus of the material.

7. The program product as recited in claim 5, wherein the signal bearing media is recordable media.

8. The program product as recited in claim 5, wherein the signal bearing media is transmission type media.

* * * * *